(12) United States Patent
Wang et al.

(10) Patent No.: US 9,731,271 B2
(45) Date of Patent: Aug. 15, 2017

(54) METHODS FOR REGENERATING SOLID ADSORBENTS

(71) Applicant: HONEYWELL INTERNATIONAL INC., Morristown, NJ (US)

(72) Inventors: Haiyou Wang, Amherst, NY (US); Hsueh Sung Tung, Getzville, NY (US); Daniel C. Merkel, Orchard Park, NY (US)

(73) Assignee: HONEYWELL INTERNATIONAL. INC., Morristown, NJ (US)

( * ) Notice: Subject to any disclaimer, the term of this patent is extended or adjusted under 35 U.S.C. 154(b) by 0 days.

(21) Appl. No.: 15/136,084

(22) Filed: Apr. 22, 2016

(65) Prior Publication Data

US 2016/0311735 A1    Oct. 27, 2016

Related U.S. Application Data (60) Provisional application No. 62/152,273, filed on Apr. 24, 2015.

(51) Int. Cl.
| | | |
|---|---|---|
| *B01J 20/18* | (2006.01) | |
| *B01J 20/34* | (2006.01) | |
| *B01J 20/20* | (2006.01) | |
| *C07C 17/38* | (2006.01) | |

(52) U.S. Cl.
CPC ............... *B01J 20/18* (2013.01); *B01J 20/20* (2013.01); *B01J 20/345* (2013.01); *C07C 17/38* (2013.01)

(58) Field of Classification Search
CPC .......... B01J 20/18; B01J 20/20; B01J 20/345; C07C 17/38
USPC .......................................................... 502/20
See application file for complete search history.

(56) References Cited

U.S. PATENT DOCUMENTS

| | | |
|---|---|---|
| 6,077,982 A | 6/2000 | Yates et al. |
| RE37,789 E | 7/2002 | Bertus et al. |
| 8,796,493 B2 | 8/2014 | Merkel et al. |
| 2004/0030204 A1 | 2/2004 | Wilmet et al. |
| 2011/0105809 A1 | 5/2011 | Devic et al. |
| 2012/0222448 A1 | 9/2012 | Chaki et al. |
| 2013/0085308 A1 | 4/2013 | Merkel et al. |
| 2015/0011803 A1 | 1/2015 | Imura et al. |

FOREIGN PATENT DOCUMENTS

| | | |
|---|---|---|
| WO | 2013049105 A1 | 4/2013 |
| WO | 2013119919 A1 | 8/2013 |

OTHER PUBLICATIONS

International Search Report and Written Opinion issued in International Application No. PCT/US2016/028755 dated Aug. 4, 2016.

*Primary Examiner* — Edward Johnson
(74) *Attorney, Agent, or Firm* — Scully, Scott, Murphy & Presser, P.C.

(57) ABSTRACT

The invention provides for a method of regenerating a solid adsorbent, such as a molecular sieve or activated carbon, using stable fluorinated hydrocarbon compounds such as, for example, HFC-245cb (1,1,1,2,2-pentafluoropropane, as a regeneration fluid.

23 Claims, 4 Drawing Sheets

METHODS FOR REGENERATING SOLID ADSORBENTS

FIELD OF THE INVENTION

The invention provides a method for regenerating solid adsorbents used to separate 2-chloro-3,3,3-trifluoropropene (HCFO-1233xf) from 2-chloro-1,1,1,2-tetrafluorpropane (HCFC-244bb), including spent solid adsorbents comprising activated carbon and molecular sieves. HCFO-1233xf can be desorbed, recovered, and recycled.

BACKGROUND OF THE INVENTION

Hydrofluoroolefins (HFOs), such as tetrafluoropropenes, including 2,3,3,3-tetrafluoropropene (HFO-1234yf), are known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and thus pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

One manufacturing process for HFO-1234yf uses 1, 1, 2, 3-tetrachloropropene (1230xa) as starting raw material. The process comprises the following three steps:

Step (1): 1230xa+3HF→2-chloro-3,3,3,-trifluoropropene (1233xf)+3 HCl in a vapor phase reactor charged with a solid catalyst, Step (2): 1233xf+HF→2-chloro-1,1,1,2-tetrafluoropropane (HCFC-244bb) in a liquid phase reactor charged with a liquid catalyst; and Step (3): 244bb→1234yf+HCl in a vapor phase reactor.

In Step (2), the conversion of 1233xf is often incomplete, and some 1233xf is carried over to Step (3) along with 244bb. The presence of 1233xf in the Step (3) feed is undesired inasmuch as it renders various advantageous recycles problematic, and raises the potential for unwanted side reactions, among other things. Separating 1233xf from 244bb is thus preferred. U.S. Published Patent Application No. 2013/0085308 relates that activated carbon, used to separate 1233xf from 244bb, can be regenerated by heating, vacuum or an inert gas stream. Regenerating the activated carbon is economically important. Nonetheless, other methods of regenerating activated carbon, and of regenerating other adsorbents useful for separating 1233xf from 244bb, are desired.

SUMMARY OF THE INVENTION

In one aspect, the invention is to a method of regenerating a solid adsorbent used in separating 2-chloro-3,3,3-trifluoropropene (HCFO-1233xf) from 2-chloro-1,1,1,2-tetrafluorpropane (HCFC-244bb), preferably a spent solid adsorbent, such as a molecular sieve or an activated carbon, using stable fluorinated hydrocarbons compounds, as regeneration fluids. In preferred embodiments, saturated hydrofluorocarbons are used as regeneration fluids. Useful examples of said fluorinated hydrocarbons included, but are not limited to, HFC-245cb (1,1,1,2,2-pentafluoropropane), HFC-245fa (1,1,1,3,3-pentafluoropropane), HCF-245eb (1,1,1,2,3-pentafluoropropane), HFC-245ea (1,1,2,3,3-pentalfuoropropane), HFC-245ca (1,1,2,2,3-pentafluoropropane), HFC-236ea (1,1,1,2,3,3-hexafluoropropane), HFC-236fa (1,1,1,3,3,3-hexafluoropropane), HFC-236cb (1,1,1,2,2,3-hexafluoropropane), HFC-236ca (1,1,2,2,3,3-hexafluoropropane), HFC-254fa (1,1,3,3-tetrafluoropropane), HFC-254fb (1,1,1,3-tetrafluoropropane), HFC-254eb (1,1,1,2-tetrafluoropropane), HFC-254cb (1,1,2,2-tetrafluoropropane), HFC-254ca (1,2,2,3-tetrafluoropropane), HFC-254ea (1,1,2,3-tetrafluoropropane), HFC-263fa (1,1,3-trifluoropropane), HFC-263fb (1,1,1-trifluoropropane), HFC-263ea (1,2,3-trifluoropropane), HFC-263eb (1,1,2-trifluoropropane), HFC-263ca (1,2,2-trifluoropropane), HFC-272fa (1,3-difluoropropane), HFC-272ea (1,2-difluoropropane), HFC-272ca (2,2-difluoropropane), HFC-272fb (1,1-difluoropropane), HFC-281fa (1-fluoropropane), HFC-281ea (2-fluoropropane), HFC-218 (octafluoropropane), HFC-227ca (1,1,1,2,2,3,3-heptafluoropropane), HFC-227ea (1,1,1,2,3,3,3-heptafluoropropane), HFC-116 (1,1,1,2,2,2-hexafluoroethane), HFC-134 (1,1,2,2-tetrafluoroethane), HFC-134a (1,1,1,2-tetrafluoroethane), HFC-125 (1,1,1,2,2-pentafluoroethane), HFC-143 (1,1,2-trifluoroethane), HFC-143a (1,1,1-trifluoroethane), HFC-152 (1,2-difluoroethane), HFC-152a (1,1-difluoroethane), HFC-161 (fluoroethane), FC-14 (tetrafluoromethane), HFC-23 (trifluoromethane), HFC-32 (difluoromethane), HFC-41 (fluoromethane), and mixtures thereof, as regeneration fluids.

DETAILED DESCRIPTION OF THE INVENTION

In one embodiment, the invention relates to a method of regenerating a solid adsorbent used in separating 2-chloro- 3,3,3-trifluoropropene (HCFO-1233xf) from 2-chloro-1,1,1,2-tetrafluorpropane (HCFC-244bb) wherein the solid adsorbent contains 2-chloro-3,3,3-trifluoropropene (HCFO-1233xf). The method of regenerating comprises contacting at least a portion of the solid adsorbent with a fluorinated hydrocarbon compound under conditions effective to desorb at least a portion of the HCFO-1233xf. Regeneration can occur at any time as known in the art, preferably when the adsorbent is at or near saturation; that is to say, when the adsorbent is spent or near being spent.

Suitable solid adsorbents include, without limitation, molecular sieves, carbon molecular sieves, and activated carbons. Molecular sieves that are serviceable in separating 2-chloro-3,3,3-trifluoropropene (HCFO-1233xf and 2-chloro-1,1,1,2-tetrafluorpropane (HCFC-244bb) include, without limitation, those having a pore size of 5 Å or greater. Such molecular sieves include, without limitation, zeolites such as 13X, ZSM-5, H-ZSM-5, MFI or silicalite (an Al-free version of ZMS-5), and combinations thereof. In a preferred practice, the pore size is 5.5 Å or greater. More preferably, the pore size is 5.5 Å to 10 Å. Other preferred pore sizes include 6 Å, 6.5 Å, 7 Å, 7.5 Å, 8 Å, 8.5 Å, 9 Å, 9.5 Å, and all ranges in between. The most preferred pore size is about 10 Å. The adsorption can occur under static or flow conditions. As used herein, the term molecular sieve includes carbon molecular sieves, such as those derived from natural materials such as coal or from man-made polymers such as discussed in U.S. Pat. Nos. 4,820,681 and 6,670,304 and US Publication No. 2002/0025290. It will be understood that the term sorb and its cognates (e.g. adsorbent) as used herein includes the act of adsorption, absorption and the like, and is not limited to any particular type of adsorption or absorption in any physical or thermodynamic sense. The term is intended to encompass whatever processes or mechanism, or combinations thereof, are present, by which HCFO-1233xf and HCFC-244bb are separated.

Carbon molecular sieves useful in the present invention include, without limitation, those derived from natural materials such as coal or from man-made polymers such as discussed in U.S. Pat. Nos. 4,820,681 and 6,670,304 and US Publication No. 2002/0025290. These carbon molecular sieves are distinguished from activated carbons, which are also derived from natural materials but have much larger pore sizes. The carbon molecular sieves useful for the separation described herein have an exemplary pore size of 5.0 Å or greater.

Serviceable activated carbons include coconut shell based activated carbon, a coal based activated carbon, or combinations thereof. In certain embodiments, the activated carbon is designed by the manufacturer for use in vapor phase applications. In certain embodiments, the activated carbon is designed by the manufacturer for use in liquid phase applications. Calgon Carbon Corporation of Pittsburgh, Pa. manufactures and sells a number of such activated carbons, including products having the following designations; BPL, RVG, OVC, COCO, AT-410, and VPR, as examples.

One parameter used to characterize activated carbons is the Iodine Number. The Iodine Number is generally used as a measure of activity level, a higher number indicates a higher degree of activation, and it also serves as an indicator of the micropore content of the activated carbon. The Iodine Number is defined as the milligrams of iodine adsorbed by one gram of carbon when the iodine concentration in the residual filtrate is 0.02 normal.

In the present invention, activated carbons having a minimum Iodine Number of 900 are expected to sorb at least a portion of the olefin impurities. Activated carbons having a minimum Iodine Number of 1000 are expected to sorb more of the olefin impurities. Activated carbons having a minimum Iodine Number of 1100 are expected to sorb even more of the olefin impurities. Finally, activated carbons having a minimum Iodine Number of 1200 are expected to sorb still more of the olefin impurities. Other solid adadsorbents having properties similar to those of the activated carbons are also expected to be useful herein.

In one practice, the fluorinated hydrocarbon compound is selected from the group consisting of HFC-245cb (1,1,1,2,2-pentafluoropropane), HFC-245fa (1,1,1,3,3-pentafluoropropane), HCF-245eb (1,1,1,2,3-pentafluoropropane), HFC-236ea (1,1,1,2,3,3-hexafluoropropane), HFC-134a (1,1,1,2-tetrafluoroethane), HFC-125 (1,1,1,2,2-pentafluoroethane), and mixtures thereof. HFC-245cb is preferred as the predominant or sole regenerating fluid. In one practice, HFC-245cb is obtained as a by-product of Step (2) shown above and can be conveniently used as the regenerating fluid. Inert gases can be used in admixture with the fluorinated hydrocarbons.

The temperature at which regeneration is below that which will cause reactions with the fluorinated organics to occur, or otherwise, but must be high enough to allow desorption to occur. For activated carbons, a preferred temperature is about 100° C. to 300° C., more preferably about 150° C. to about 250° C. When the adsorbent is a molecular sieve as described herein the temperature is preferably about 50° C. to about 250° C., more preferably about 100° C. to about 200° C.

In another embodiment, the HCFO-1233xf can be desorbed by techniques known in the art, for example, by degassing, including by vacuum. The desorbed HCFO-1233xf can be collected afterward and repurposed, such as recycle. In certain practices, the desorbed HCFO-1233xf also comprises at least a portion of the fluorinated organic compound used for regeneration. The desorbed HCFO-1233xf can be separated from this fluorinated organic compound, for example by distillation, and the HCFO-1233xf thereafter recovered. All or a portion of the recovered HCFO-1233xf can be recycled, for example, back to Step (2) of the HFO-1234yf process shown above.

The another embodiment, the invention is to a method of preparing 2,3,3,3-tetrafluoropropene (HFO-1234yf) comprising contacting a first intermediate composition comprising 2-chloro-3,3,3-trifluoropropene (HCFO-1233xf) with HF in the presence of a fluorination catalyst under conditions effective to produce a second intermediate composition comprising 2-chloro-1,1,1,2-tetrafluorpropane (HCFC-244bb) and unreacted HCFO-1233xf; separating the unreacted HCFO-1233xf from the HCFC-244bb by contacting the second intermediate composition with a solid adsorbent under conditions effective such that the solid adsorbent sorbs the unreacted HCFO-1233xf thereby separating it from at least a portion of the HCFC-244bb; regenerating the solid sorbent by contacting the solid sorbent with a fluorinated hydrocarbon compound under conditions effective to desorb at least a portion of the HCFO-1233xf; and dehydrochlorinating at least a portion of the HCFC-244bb separated in step (b) to produce a reaction product comprising HFO-1234yf.

The following examples are illustrative only and are not limiting to the present invention.

Example 1

A cylindrical Monel reactor of ¾" diameter immersed into a 3-zone electrical furnace was used in all of the experiments of adsorption tests. Process temperatures were recorded using a multi-point thermocouple placed inside the reactor and within the solid adsorbent bed. The distance between two adjacent probe points was 4". The solid adsorbent was loaded in such a way that its bed was within three adjacent probe points. The solid adsorbent was dried in nitrogen flow for 4 hours at 200° C. After drying step, the reactor was cooled down to room temperature (typically between 20° and 30° C.). 244bb feed was then fed into the bottom of the vertically mounted reactor and was vaporized before reaching the bed of solid adsorbent. Effluent gases were periodically analyzed by means of gas chromatograph (GC) to determine the adsorption efficiency of each adsorbent.

Various molecular sieves were tested for adsorbing 1233xf included in 244bb feed with a 244bb feed containing 2.304 GC area% 1233xf. The capacity of each adsorbent was calculated based on individual isothermal adsorption curve and the results are presented in Table 1. The molecular sieve 13X showed the highest adsorption capacity (ca. 1.6 wt % of its own weight). Table 2 presents the performance of 13X. During the effective period of time (where the adsorption percentage of 1233xf was >95%), the 1233xf concentration in effluent stream was below 1000 ppm.

Example 2

The same set-up and procedure as in Example 1 were used in Example 2. Various activated carbons (AC) were tested for adsorbing 1233xf included in 244bb feed with a 244bb feed containing 2.304 GC area% 1233xf. The capacity of each adsorbent was calculated based on individual isothermal adsorption curve and the results are presented in Table 3. Calgon OLC 12X40 AC showed the highest adsorption capacity (ca. 5.3 wt % of its own weight). Table 4 presents the performance of Calgon OLC 12X40 AC. During the effective period of time (where the adsorption percentage of 1233xf was >95%), the 1233xf concentration in effluent stream was below 1000 ppm.

TABLE 1

Capacity of various molecular sieves for adsorbing 1233xf at room temperature and atmosphere pressure*

| Adsorbent | Capacity, g-1233xf/ml-adsorbent | Capacity, g-1233xf/g-adsorbent |
| --- | --- | --- |
| 5A | <0.0001 | <0.0001 |
| AW-500 | 0.0003 | 0.0004 |
| MFI(40)-6 ($H^+$ form) | 0.0033 | 0.0046 |
| MFI(300)-6 ($H^+$-silicalite) | 0.0015 | 0.0024 |
| MFI(550)-5 ($Na^+$-silicalite) | 0.0021 | 0.0030 |
| ZSM-5 ($SiO_2/Al_2O_3$ mole ratio = 50) | 0.0028 | 0.0045 |
| H-ZSM-5 ($SiO_2/Al_2O_3$ mole ratio = 280) | 0.0012 | 0.0019 |
| 13X | 0.0129 | 0.0159 |

*Feed composition: 97.6957 GC area % 244bb/2.3043 GC area % 1233xf; 50 ml of adsorbent

TABLE 3

Capacity of various carbons for adsorbing 1233xf at room temperature and atmosphere pressure

| Adsorbent | Capacity, g-1233xf/ml-adsorbent | Capacity, g-1233xf/g-adsorbent |
| --- | --- | --- |
| Calgon AC (CPG-LF) | 0.0224 | 0.0438 |
| Norit ROX | 0.0185 | 0.0472 |
| Calgon OVC 4X8 | 0.0192 | 0.0448 |
| Calgon 207C 6X15 | 0.0111 | 0.0260 |
| Calgon WS-480 | 0.0106 | 0.0257 |
| Calgon OLC 12X30 | 0.0216 | 0.0392 |
| Calgon OLC 12X40 | 0.0276 | 0.0530 |

TABLE 2

Performance of 13X molecular sieve during 1233xf adsorption at room temperature and atmosphere pressure*

| Period of time, h | Feed passed through, g | Reactor effluent composition, GC area % | | | 1233xf adsorbed, % | 1233xf adsorbed, g |
| --- | --- | --- | --- | --- | --- | --- |
| | | 1234yf | 244bb | 1233xf | | |
| 0-1 | 0.6 | 0.0000 | 100.0000 | 0.0000 | 100.0 | 0.0138 |
| 1-2 | 9.6 | 0.0000 | 100.0000 | 0.0000 | 100.0 | 0.2212 |
| 2-3 | 3.7 | 0.0157 | 99.9608 | 0.0235 | 99.0 | 0.0844 |
| 3-4 | 5.7 | 0.0202 | 99.9170 | 0.0628 | 97.3 | 0.1278 |
| 4-5 | 5.5 | 0.0190 | 99.1041 | 0.8769 | 61.9 | 0.0785 |
| 5-6 | 5.4 | 0.0148 | 97.9563 | 2.0288 | 12.0 | 0.0149 |
| 6-7 | 5.6 | 0.0188 | 97.7267 | 2.2545 | 2.2 | 0.0028 |
| 7-8 | 5.2 | 0.0240 | 97.7792 | 2.1968 | 4.7 | 0.0056 |
| 8-9 | 5.4 | 0.0246 | 97.7901 | 2.1853 | 5.2 | 0.0064 |

*Feed composition: 97.6957 GC area % 244bb/2.3043 GC area % 1233xf; 50 ml of adsorbent

TABLE 4

Performance of Calgon OLC 12X40 AC during 1233xf adsorption at room temperature and atmosphere pressure*

| Period of time, h | Feed passed through, g | Reactor effluent composition, GC area % | | | 1233xf adsorbed, % | 1233xf adsorbed, g |
|---|---|---|---|---|---|---|
| | | 1234yf | 244bb | 1233xf | | |
| 0-1 | 0.2 | 0.00 | 97.4645 | 2.5355 | 0.0 | 0.0000 |
| 1-2 | 1.7 | 0.00 | 99.6228 | 0.3772 | 83.6 | 0.0328 |
| 2-3 | 6.0 | 0.00 | 100.0000 | 0.0000 | 100.0 | 0.1383 |
| 3-4 | 5.0 | 0.00 | 99.9019 | 0.0981 | 95.7 | 0.1103 |
| 4-5 | 5.2 | 0.00 | 100.00 | 0.00 | 100.0 | 0.1198 |
| 5-6 | 5.3 | 0.00 | 100.00 | 0.00 | 100.0 | 0.1221 |
| 6-7 | 5.2 | 0.00 | 100.00 | 0.00 | 100.0 | 0.1198 |
| 7-8 | 5.5 | 0.00 | 100.00 | 0.00 | 100.0 | 0.1267 |
| 8-9 | 5.2 | 0.00 | 100.00 | 0.00 | 100.0 | 0.1198 |
| 9-10 | 5.2 | 0.00 | 100.00 | 0.00 | 100.0 | 0.1198 |
| 10-11 | 5.1 | 0.0161 | 99.9839 | 0.00 | 100.0 | 0.1175 |
| 11-12 | 5.2 | 0.0591 | 99.8635 | 0.0775 | 96.6 | 0.1158 |
| 12-13 | 5.2 | 0.0167 | 98.5792 | 1.4041 | 39.1 | 0.0468 |
| 13-14 | 5.3 | 0.0082 | 98.0500 | 1.9418 | 15.7 | 0.0192 |
| 14-15 | 5.1 | 0.0067 | 97.9688 | 2.0245 | 12.1 | 0.0143 |
| 15-16 | 5.1 | 0.0058 | 97.9276 | 2.0666 | 10.3 | 0.0121 |
| 16-17 | 5.4 | 0.0053 | 97.7773 | 2.0891 | 9.3 | 0.0116 |
| 17-18 | 5.3 | 0.0053 | 97.8879 | 2.1067 | 8.6 | 0.0105 |
| 18-19 | 5.2 | 0.0047 | 97.8258 | 2.1695 | 5.8 | 0.0070 |
| 19-20 | 5.5 | 0.0049 | 97.7875 | 2.2076 | 4.2 | 0.0053 |
| 20-21 | 5.2 | 0.0047 | 97.7436 | 2.2516 | 2.3 | 0.0027 |
| 21-22 | 5.3 | 0.0042 | 97.7569 | 2.2389 | 2.8 | 0.0035 |
| 22-23 | 5.2 | 0.0042 | 97.7495 | 2.2463 | 2.5 | 0.0030 |

*Feed composition: 97.6957 GC area % 244bb/2.3043 GC area % 1233xf; 50 ml of adsorbent Example 3

A cylindrical Monel reactor of ¾" diameter immersed into a 3-zone electrical furnace was used in this adsorption tests using carbon molecular sieves. Process temperatures were recorded using a multi-point thermocouple placed inside the reactor and within the solid adsorbent bed. The distance between two adjacent probe points was 4". The solid adsorbent was loaded in such a way that its bed was within three adjacent probe points. The solid adsorbent was dried in nitrogen flow for 4 hours at 200° C. After drying step, the reactor was cooled down to room temperature (typically between 20° and 30° C.). 244bb feed was then fed into the bottom of the vertically mounted reactor and was vaporized before reaching the bed of solid adsorbent. Effluent gases were periodically analyzed by means of gas chromatograph (GC) to determine the adsorption efficiency of each adsorbent. Various carbon molecular sieves were tested for adsorbing 1233xf included in 244bb feed with a 244bb feed containing 2.3043 GC area % 1233xf. The capacity of each adsorbent was calculated based on individual isothermal adsorption curve and the results are presented in Table 5. The X2M4/6 showed the highest adsorption capacity (ca. 6.2 wt % of its own weight). Table 6 presents the performance of X2M4/6 carbon molecular sieve. During the effective period of time (where the adsorption percentage of 1233xf was >95%), the 1233xf concentration in effluent stream was below 1000 ppm.

TABLE 5

Capacity of various carbon molecular sieves for adsorbing 1233xf at room temperature and atmosphere pressure*

| Adsorbent | Surface area, m²/g | Pore volume, ml/g | Average pore size, Å | Capacity, g-1233xf/ml-adsorbent | Capacity, g-1233xf/g-adsorbent |
|---|---|---|---|---|---|
| X2M4/6 | 508.1 | 0.23 | 17.8 | 0.0318 | 0.0615 |
| CMS H255/2 | 750 | 0.3 | 5 | 0.0286 | 0.0494 |
| Shirasagi CT-350 | 300 | 0.1 | 3 | <0.0001 | <0.0001 |

*Feed composition: 97.6957 GC area % 244bb/2.3043 GC area % 1233xf; 50 ml of adsorbent

TABLE 6

Performance of X2M4/6 carbon molecular sieve during 1233xf adsorption at room temperature and atmosphere pressure*

| Period of time, h | Feed passed through, g | Reactor effluent composition, GC area % | | | 1233xf adsorbed, % | 1233xf adsorbed, g |
|---|---|---|---|---|---|---|
| | | 1234yf | 244bb | 1233xf | | |
| 0-1 | 4.9 | 0.0000 | 99.9324 | 0.0676 | 96.5348 | 0.1000 |
| 1-2 | 5.1 | 0.0000 | 100.0000 | 0.0000 | 100.0000 | 0.1078 |
| 2-3 | 5.0 | 0.0074 | 99.9926 | 0.0000 | 100.0000 | 0.1057 |
| 3-4 | 5.0 | 0.0000 | 100.0000 | 0.0000 | 100.0000 | 0.1057 |
| 4-5 | 4.9 | 0.0029 | 99.9940 | 0.0032 | 99.8360 | 0.1034 |
| 5-6 | 5.1 | 0.0065 | 99.9816 | 0.0119 | 99.3900 | 0.1071 |
| 6-7 | 5.0 | 0.0133 | 99.9467 | 0.0400 | 97.9496 | 0.1035 |

TABLE 6-continued

Performance of X2M4/6 carbon molecular sieve during 1233xf
adsorption at room temperature and atmosphere pressure*

| Period of time, h | Feed passed through, g | Reactor effluent composition, GC area % | | | 1233xf adsorbed, % | 1233xf adsorbed, g |
|---|---|---|---|---|---|---|
| | | 1234yf | 244bb | 1233xf | | |
| 7-8 | 5.1 | 0.0250 | 99.8642 | 0.1108 | 94.3203 | 0.1017 |
| 8-9 | 5.1 | 0.0325 | 99.7882 | 0.1793 | 90.8089 | 0.0979 |
| 9-10 | 5.1 | 0.0369 | 99.5314 | 0.4316 | 77.8757 | 0.0840 |
| 10-11 | 4.9 | 0.0474 | 99.2961 | 0.6566 | 66.3420 | 0.0687 |
| 11-12 | 4.9 | 0.0478 | 98.911 | 1.0412 | 46.6270 | 0.0483 |
| 12-13 | 4.9 | 0.0419 | 98.6312 | 1.3269 | 31.9818 | 0.0331 |
| 13-14 | 5.1 | 0.0381 | 98.511 | 1.4509 | 25.6254 | 0.0276 |
| 14-15 | 4.9 | 0.0336 | 98.363 | 1.6034 | 17.8081 | 0.0184 |
| 15-16 | 5.0 | 0.0301 | 98.2906 | 1.6793 | 13.9174 | 0.0147 |
| 16-17 | 5.0 | 0.0278 | 98.2391 | 1.7331 | 11.1595 | 0.0118 |
| 17-18 | 5.1 | 0.0259 | 98.1925 | 1.7815 | 8.6785 | 0.0094 |
| 18-19 | 5.1 | 0.0244 | 98.1692 | 1.8065 | 7.3970 | 0.0080 |
| 19-20 | 5.1 | 0.0254 | 98.1349 | 1.8397 | 5.6951 | 0.0061 |
| 20-21 | 5.0 | 0.0237 | 98.125 | 1.8512 | 5.1056 | 0.0054 |
| 21-22 | 5.1 | 0.0242 | 98.1068 | 1.8689 | 4.1983 | 0.0045 |
| 22-23 | 5.1 | 0.0231 | 98.0325 | 1.9444 | 0.3281 | 0.0004 |

*Feed composition: 97.6957 GC area % 244bb/2.3043 GC area % 1233xf; 40 ml of adsorbent Example 4

Figure 1:
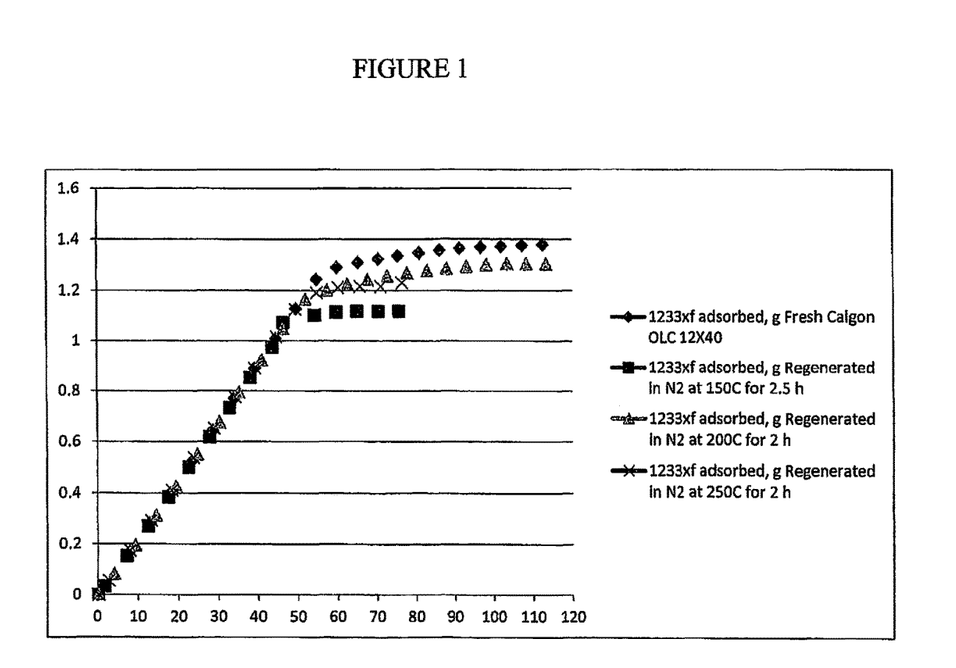
FIG. 1 graphically depicts the comparative performance of fresh and regenerated activated carbon (Calgon OLC 12X40) for 1233xf adsoption where the regeneration is by nitrogen purge gas at 150° C., 200° C., and 250° C. for the time frames indicated. (Feed composition: 97.6957 GC area % 244bb/2.3043 GC area % 1233xf; 50 ml of adsorbent; room temperature; atmosphere pressure)

After reaching adsorption saturation over the Calgon OLC 12X40 AC in Example 2, the regeneration of the spent Calgon OLC 12X40 AC was first conducted in nitrogen flow by ramping temperature to 150° C. and holding at the same temperature for 2.5 h. After regeneration and cool down, the adsorption experiment was re-started at room temperature. The regeneration at 200° C. and 250° C. was done similarly. As shown in FIG. 1, the spent AC was regenerable with $N_2$ as purging gas and required a temperature>200° C.

Example 5

Figure 2:
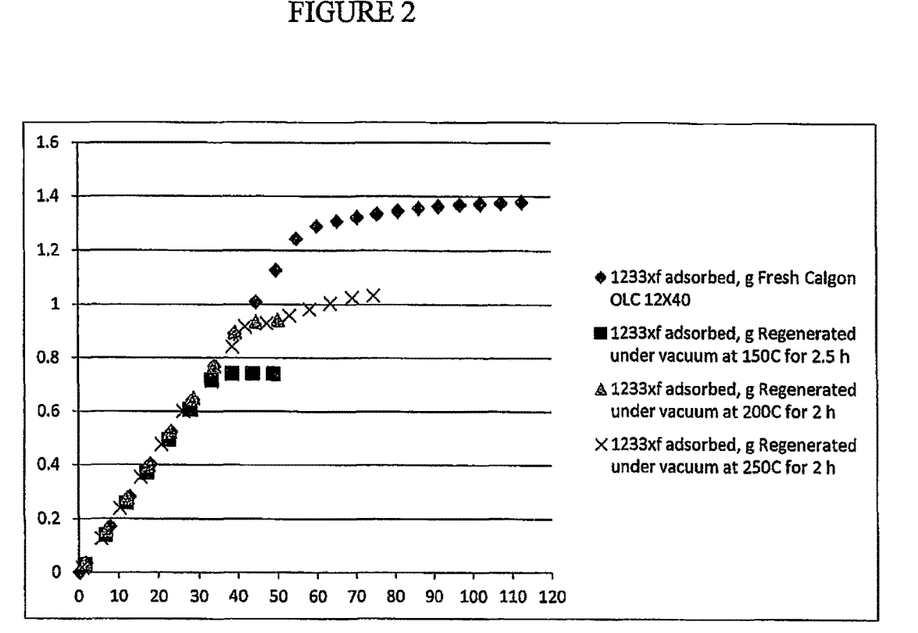
FIG. 2 graphically depicts the comparative performance of fresh and regenerated activated carbon (Calgon OLC 12X40) for 1233xf adsoption where the regeneration is by vacuum at 150° C., 200° C., and 250° C. at the time frames indicated. (Feed composition: 97.6957 GC area% 244bb/2.3043 GC area% 1233xf; 50 ml of adsorbent; room temperature; atmosphere pressure)

One issue associated with using nitrogen as purging gas for regeneration is the material loss during the recovery of adsorbed 244bb and 1233xf due to its difficulty to be condensed. Regeneration of the spent Calgon OLC 12X40 AC was then conducted under vacuum by ramping temperature to 150° C., 200° C., or 250° C. and holding at the same temperature for an extended period of time. A YELLOW JACKET Pump (Model 93540), which can pull a vacuum down to 15 microns, was used to pull the vacuum. As shown in FIG. 2, the linear increase period for 1233xf adsorption was shorter after the regeneration under vacuum than that after the regeneration in nitrogen flow. Nevertheless, similar to the regeneration with $N_2$ as purging gas, the regeneration under vacuum required a temperature>200° C. as well.

Example 6

Figure 3:
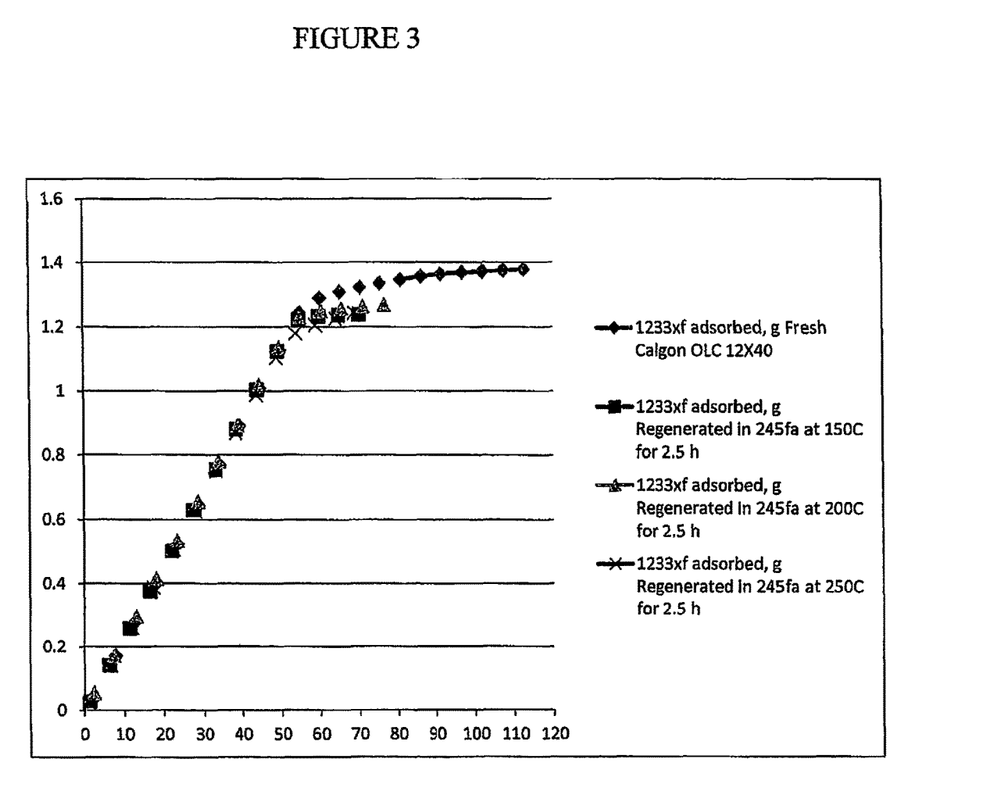
FIG. 3 graphically depicts the comparative performance of fresh and regenerated activated carbon (Calgon OLC 12X40) for 1233xf adsoption where the regeneration is by the organic 1,1,1,3,3-pentafluoropropane (245fa) purge at 150° C., 200° C., and 250° C. at the time frames indicated (Feed composition: 97.6957 GC area% 244bb/2.3043 GC area % 1233xf; 50 ml of adsorbent; room temperature; atmosphere pressure).

A regeneration method was used, in which purging (desorption) step was conducted with 1,1,1,3,3-pentafluoropropane (245fa) as purging agent. As shown in FIG. 3, the length of the linear increase period for 1233xf adsorption after regeneration in 245fa flow at each of three temperatures (150° C., 200° C., and 250° C.) tested was almost the same as the fresh activated carbon. This indicates after each cycle of regeneration, the length of operation time is almost the same as the fresh activated carbon.

Example 7

Figure 4:
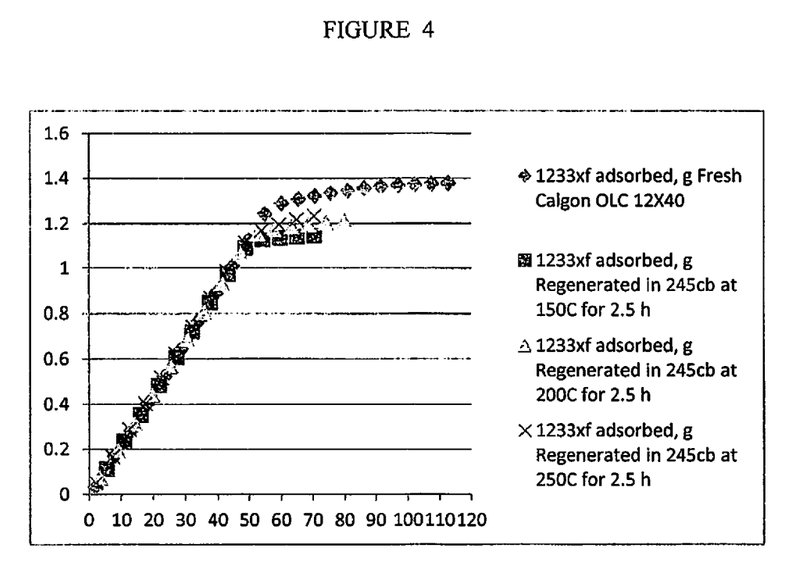
FIG. 4 graphically depicts the comparative performance of fresh and regenerated activated carbon (Calgon OLC 12X40) for 1233xf adsoption where the regeneration is by the organic 1,1,1,2,2-pentafluoropropane (245cb) purge at 150° C., 200° C., and 250° C. at the time frames indicated (Feed composition: 97.6957 GC area% 244bb/2.3043 GC area% 1233xf; 50 ml of adsorbent; room temperature; atmosphere pressure).

A regeneration method was used, in which purging (desorption) step was conducted with 1,1,1,2,2-pentafluoropropane (245cb) as purging agent. As shown in FIG. 4, the length of the linear increase period for 1233xf adsorption after regeneration in 245cb flow at each of three temperatures (150° C., 200° C., and 250° C.) tested was almost the same as the fresh activated carbon. This indicates after each cycle of regeneration, the length of operation time is almost the same as the fresh activated carbon. Other hydrofluorocarbons such as 245eb, 236ea, 125, 134a are used as purging gases during regeneration, and similar results are achieved. Table 7 presents the performance of regenerated Calgon OLC 12X40 AC. One can see during the effective period of time (where the adsorption percentage of 1233xf was >95%), the 1233xf concentration in effluent stream was below 1000 ppm.

TABLE 7

Performance of regenerated Calgon OLC 12X40 AC during 1233xf
adsorption at room temperature and atmosphere pressure*

| Regeneration temp., ° C. | Period of time, h | Feed passed through, g | Reactor effluent composition, GC area % | | | 1233xf adsorbed, % | 1233xf adsorbed, g |
|---|---|---|---|---|---|---|---|
| | | | 1234yf | 244bb | 1233xf | | |
| 150 | 0-1 | 0.6 | 3.6650 | 93.8473 | 2.4878 | 0.0000 | 0.0000 |
| | 1-2 | 4.9 | 0.0363 | 99.9520 | 0.0117 | 99.4923 | 0.1123 |
| | 2-3 | 5.4 | 0.0176 | 99.9748 | 0.0076 | 99.6702 | 0.1240 |
| | 3-4 | 5.1 | 0.0196 | 99.9676 | 0.0128 | 99.4445 | 0.1169 |
| | 4-5 | 5.7 | 0.0071 | 99.9637 | 0.0292 | 98.7328 | 0.1297 |
| | 5-6 | 5.4 | 0.0052 | 99.9911 | 0.0038 | 99.8351 | 0.1242 |

TABLE 7-continued

Performance of regenerated Calgon OLC 12X40 AC during 1233xf adsorption at room temperature and atmosphere pressure*

| Regeneration temp., °C. | Period of time, h | Feed passed through, g | Reactor effluent composition, GC area % | | | 1233xf adsorbed, % | 1233xf adsorbed, g |
|---|---|---|---|---|---|---|---|
| | | | 1234yf | 244bb | 1233xf | | |
| | 6-7 | 4.9 | 0.0055 | 99.9904 | 0.0041 | 99.8221 | 0.1127 |
| | 7-8 | 5.6 | 0.0051 | 99.9949 | 0.0000 | 100.0000 | 0.1290 |
| | 8-9 | 5.5 | 0.0056 | 99.9944 | 0.0000 | 100.0000 | 0.1267 |
| | 9-10 | 5.5 | 0.0060 | 98.0910 | 0.1849 | 91.9759 | 0.1166 |
| | 10-11 | 5.4 | 0.0036 | 98.3491 | 1.6473 | 28.5119 | 0.0355 |
| | 11-12 | 5.6 | 0.0025 | 97.8440 | 2.1535 | 6.5443 | 0.0084 |
| | 12-13 | 5.3 | 0.0000 | 97.8126 | 2.1862 | 5.1252 | 0.0063 |
| | 13-14 | 5.3 | 0.0000 | 97.7811 | 2.2189 | 3.7061 | 0.0045 |
| 200 | 0-1 | 3.4 | 0.9372 | 98.9511 | 0.1117 | 95.1525 | 0.0745 |
| | 1-2 | 5.5 | 0.4447 | 99.4409 | 0.1145 | 95.0310 | 0.1204 |
| | 2-3 | 5.3 | 0.0110 | 99.9572 | 0.0319 | 98.6156 | 0.1204 |
| | 3-4 | 5.5 | 0.0375 | 99.9555 | 0.0070 | 99.6962 | 0.1264 |
| | 4-5 | 5.6 | 0.2150 | 99.9597 | 0.0188 | 99.1841 | 0.1280 |
| | 5-6 | 5.2 | 0.0069 | 99.9595 | 0.0338 | 98.5332 | 0.1181 |
| | 6-7 | 5.2 | 0.0075 | 99.9888 | 0.0037 | 99.8394 | 0.1196 |
| | 7-8 | 5.6 | 0.0090 | 99.9458 | 0.0451 | 98.0428 | 0.1265 |
| | 8-9 | 5.8 | 0.0114 | 99.9854 | 0.0032 | 99.8611 | 0.1335 |
| | 9-10 | 5.3 | 0.0097 | 99.3474 | 0.6429 | 72.1000 | 0.0881 |
| | 10-11 | 5.2 | 0.0055 | 98.0420 | 1.9524 | 15.2714 | 0.0183 |
| | 11-12 | 5.6 | 0.0045 | 97.9183 | 2.0773 | 9.8511 | 0.0127 |
| | 12-13 | 5.2 | 0.0041 | 97.8986 | 2.0973 | 8.9832 | 0.0108 |
| | 13-14 | 5.7 | 0.0033 | 97.8205 | 2.1761 | 5.5635 | 0.0073 |
| | 14-15 | 5.7 | 0.0028 | 97.8411 | 2.1561 | 6.4315 | 0.0084 |
| 250 | 0-1 | 2.2 | 0.0390 | 99.8529 | 0.0328 | 98.5766 | 0.0000 |
| | 1-2 | 5.1 | 0.0206 | 99.9489 | 0.0122 | 99.4706 | 0.0504 |
| | 2-3 | 5.2 | 0.0200 | 99.9727 | 0.0067 | 99.7092 | 0.1172 |
| | 3-4 | 5.0 | 0.0164 | 99.9800 | 0.0000 | 100.0000 | 0.1198 |
| | 4-5 | 5.0 | 0.0120 | 99.9836 | 0.0000 | 100.0000 | 0.1152 |
| | 5-6 | 4.5 | 0.0090 | 99.9880 | 0.0000 | 100.0000 | 0.1152 |
| | 6-7 | 5.2 | 0.0090 | 99.9910 | 0.0000 | 100.0000 | 0.1037 |
| | 7-8 | 5.5 | 0.0073 | 99.9910 | 0.0000 | 100.0000 | 0.1198 |
| | 8-9 | 5.1 | 0.0067 | 99.9927 | 0.0000 | 100.0000 | 0.1267 |
| | 9-10 | 5.7 | 0.0081 | 99.9933 | 0.0000 | 100.0000 | 0.1175 |
| | 10-11 | 5.3 | 0.0055 | 99.9537 | 0.0382 | 98.3422 | 0.1292 |
| | 11-12 | 5.4 | 0.0042 | 98.7224 | 1.2721 | 44.7945 | 0.0547 |
| | 12-13 | 5.5 | 0.0038 | 98.1693 | 1.8265 | 20.7351 | 0.0258 |
| | 13-14 | 5.5 | 0.0034 | 98.1138 | 1.8824 | 18.3092 | 0.0232 |

*Feed composition: 97.6957 GC area % 244bb/2.3043 GC area % 1233xf; 50 ml of adsorbent The foregoing description is by way of example only and is not limiting to the scope of the invention.

What is claimed is:

1. A method of regenerating a solid adsorbent containing 2-chloro-3,3,3-trifluoropropene (HCFO-1233xf) comprising contacting at least a portion of the solid adsorbent with a fluorinated hydrocarbon compound under conditions effective to desorb at least a portion of the HCFO-1233xf.

2. The method of claim 1 wherein the fluorinated hydrocarbon compound is selected from the group consisting of HFC-245cb (1,1,1,2,2-pentafluoropropane), HFC-245fa (1,1,1,3,3-pentafluoropropane), HCF-245eb (1,1,1,2,3-pentafluoropropane), HFC-245ea (1,1,2,3,3-pentalfuoropropane), HFC-245ca (1,1,2,2,3-pentafluoropropane), HFC-236ea (1,1,1,2,3,3-hexafluoropropane), HFC-236fa (1,1,1,3,3,3-hexafluoropropane), HFC-236cb (1,1,1,2,2,3-hexafluoropropane), HFC-236ca (1,1,2,2,3,3-hexafluoropropane), HFC-254fa (1,1,3,3-tetrafluoropropane), HFC-254fb (1,1,1,3-tetrafluoropropane), HFC-254eb (1,1,1,2-tetrafluoropropane), HFC-254cb (1,1,2,2-tetrafluoropropane), HFC-254ca (1,2,2,3-tetrafluoropropane), HFC-254ea (1,1,2,3-tetrafluoropropane), HFC-263fa (1,1,3-trifluoropropane), HFC-263fb (1,1,1-trifluoropropane), HFC-263ea (1,2,3-trifluoropropane), HFC-263eb (1,1,2-trifluoropropane), HFC-263ca (1,2,2-trifluoropropane), HFC-272fa (1,3-difluoropropane), HFC-272ea (1,2-difluoropropane), HFC-272ca (2,2-difluoropropane), HFC-272fb (1,1-difluoropropane), HFC-281fa (1-fluoropropane), HFC-281ea (2-fluoropropane), HFC-218 (octafluoropropane), HFC-227ca (1,1,1,2,2,3,3-heptafluoropropane), HFC-227ea (1,1,1,2,3,3,3-heptafluoropropane), HFC-116 (1,1,1,2,2,2-hexafluoroethane), HFC-134 (1,1,2,2-tetrafluoroethane), HFC-134a (1,1,1,2-tetrafluoroethane), HFC-125 (1,1,1,2,2-pentafluoroethane), HFC-143 (1,1,2-trifluoroethane), HFC-143a (1,1,1-trifluoroethane), HFC-152 (1,2-difluoroethane), HFC-152a (1,1-difluoroethane), HFC-161 (fluoroethane), FC-14 (tetrafluoromethane), HFC-23 (trifluoromethane), HFC-32 (difluoromethane), HFC-41 (fluoromethane), and mixtures thereof.

3. The method of claim 2 wherein the fluorinated hydrocarbon compound is HFC-245cb, HFC-245fa, or mixtures thereof.

4. The method of claim 1 wherein the solid adsorbent is a molecular sieve having a pore size of 5 Å or greater.

5. The method of claim 4 wherein the pore size is 5.5 Å or greater.

6. The method of claim 5 wherein the pore size is 5.5 Å to 10 Å.

7. The method of claim 4 wherein the molecular sieve is a zeolite selected from the group consisting of 13X, ZSM-5, H-ZSM-5, MFI, silicalite, and combinations thereof.

8. The method of claim 1 wherein the solid adsorbent is an activated carbon.

9. The method of claim 8 wherein the activated carbon has a minimum iodine number in the range of 900 to 1200.

10. The method of claim 9 wherein the activated carbon is selected from the group consisting of a coconut shell based carbon, a coal based carbon, or combinations thereof.

11. A method of preparing 2,3,3,3-tetrafluoropropene (HFO-1234yf) comprising:
   (a) contacting a first intermediate composition comprising 2-chloro-3,3,3-trifluoropropene (HCFO-1233xf) with HF in the presence of a fluorination catalyst under conditions effective to produce a second intermediate composition comprising 2-chloro-1,1,1,2-tetrafluoropropane (HCFC-244bb) and unreacted HCFO-1233xf;
   (b) separating the unreacted HCFO-1233xf from the HCFC-244bb by contacting the second intermediate composition with a solid adsorbent under conditions effective to sorb;
   the unreacted HCFO-1233xf thereby separating it from at least a portion of the HC FC-244bb;
   (c) regenerating the solid sorbent by contacting the solid sorbent with a fluorinated hydrocarbon compound under conditions effective to desorb at least a portion of the unreacted HCFO-1233xf from the solid adsorbent; and
   (c) dehydrochlorinating at least a portion of the 244bb separated in step (b) to produce a reaction product comprising HFO-1234yf.

12. The method of claim 11 wherein the solid adsorbent is a molecular sieve, a carbon molecular sieve, or an activated carbon.

13. The method of claim 12 wherein the molecular sieve has a pore size of 5 Å or greater.

14. The method of claim 13 wherein the molecular sieve is a zeolite selected from the group consisting of 13X, ZSM-5, H-ZSM-5, MFI, silicalite, and combinations thereof.

15. The method of claim 11 wherein the solid adsorbent is an activated carbon having a minimum iodine number in the range of 900 to 1200.

16. The method of claim 15 wherein the activated carbon is selected from the group consisting of a coconut shell based carbon, a coal based carbon, or combinations thereof.

17. The method of claim 11 wherein the fluorinated hydrocarbon compound is selected from the group consisting of HFC-245cb (1,1,1,2,2-pentafluoropropane), HFC-245fa (1,1,1,3,3-pentafluoropropane), HCF-245eb (1,1,1,2,3-pentafluoropropane), HFC-245ea (1,1,2,3,3-pentalfuoropropane), HFC-245ca (1,1,2,2,3-pentafluoropropane), HFC-236ea (1,1,1,2,3,3-hexafluoropropane), HFC-236fa (1,1,1,3,3,3-hexafluoropropane), HFC-236cb (1,1,1,2,2,3-hexafluoropropane), HFC-236ca (1,1,2,2,3,3-hexafluoropropane), HFC-254fa (1,1,3,3-tetrafluoropropane), HFC-254fb (1,1,1,3-tetrafluoropropane), HFC-254eb (1,1,1,2-tetrafluoropropane), HFC-254cb (1,1,2,2-tetrafluoropropane), HFC-254ca (1,2,2,3-tetrafluoropropane), HFC-254ea (1,1,2,3-tetrafluoropropane), HFC-263fa (1,1,3-trifluoropropane), HFC-263fb (1,1,1-trifluoropropane), HFC-263ea (1,2,3-trifluoropropane), HFC-263eb (1,1,2-trifluoropropane), HFC-263ca (1,2,2-trifluoropropane), HFC-272fa (1,3-difluoropropane), HFC-272ea (1,2-difluoropropane), HFC-272ca (2,2-difluoropropane), HFC-272fb (1,1-difluoropropane), HFC-281 fa (1-fluoropropane), HFC-281ea (2-fluoropropane), HFC-218 (octafluoropropane), HFC-227ca (1,1,1,2,2,3,3-heptafluoropropane), HFC-227ea (1,1,1,2,3,3,3-heptafluoropropane), HFC-116 (1,1,1,2,2,2-hexafluoroethane), HFC-134 (1,1,2,2-tetrafluoroethane), HFC-134a (1,1,1,2-tetrafluoroethane), HFC-125 (1,1,1,2,2-pentafluoroethane), HFC-143 (1,1,2-trifluoroethane), HFC-143a (1,1,1-trifluoroethane), HFC-152 (1,2-difluoroethane), HFC-152a (1,1-difluoroethane), HFC-161 (fluoroethane), FC-14 (tetrafluoromethane), HFC-23 (trifluoromethane), HFC-32 (difluoromethane), HFC-41 (fluoromethane), and mixtures thereof.

18. The method of claim 17 wherein the fluorinated hydrocarbon compound is HFC-245cb, HFC-245fa, or mixtures thereof.

19. The method of claim 11 further comprising collecting the desorbed HCFO-1233xf from step (c).

20. The method of claim 19 wherein the desorbed HCFO-1233xf that is collected comprises at least a portion of the fluorinated hydrocarbon compound used for regeneration of the solid adsorbent.

21. The method of claim 20 further comprising separating the desorbed HCFO-1233xf from the fluorinated hydrocarbon compound, and recovering at least a portion of the HCFO-1233xf that is separated.

22. The method of claim 21 wherein at least a portion of the recovered HCFO-1233xf is recycled back to step (a).

23. The method of claim 1 wherein the solid adsorbent is a carbon molecular sieve.

* * * * *